(12) United States Patent
Bjornvad et al.

(10) Patent No.: US 6,326,206 B1
(45) Date of Patent: Dec. 4, 2001

(54) IN VIVO RECOMBINATION

(75) Inventors: Mads Eskelund Bjornvad, Frederiksberg; Michael Dolberg Rasmussen, Vallensbaek; Per Lina Jorgensen, Kobenhavn; Torben Vedel Borchert, Copenhagen, all of (DK); Stanislas Dusko Ehrlich, Paris (FR)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/329,920

(22) Filed: Jun. 10, 1999

Related U.S. Application Data

(63) Continuation of application No. PCT/DK97/00567, filed on Dec. 15, 1997.
(60) Provisional application No. 60/050,590, filed on Jun. 24, 1997.

(30) Foreign Application Priority Data

Dec. 20, 1996 (DK) .................................... 1471/96
May 23, 1997 (DK) .................................... 0592/37
Aug. 14, 1997 (DK) .................................... 0935/97

(51) Int. Cl.[7] ......................... C12N 15/74; C12N 15/70; C12N 15/79

(52) U.S. Cl. .................... 435/471; 435/463; 435/468; 435/477

(58) Field of Search .................... 435/91.4, 455, 435/463, 468, 471, 476, 477

(56) References Cited

U.S. PATENT DOCUMENTS 5,521,077    5/1996    Khosla et al. .

FOREIGN PATENT DOCUMENTS 0 943 923 AA1WO    5/1987    (SE) .
97/35966            10/1997   (WO) .

OTHER PUBLICATIONS

Stemmer, Biotech., vol. 13, pp. 549–553 (Jun. 1995).
Chalfie, et al., Science, vol. 263, pp. 802–805 (Feb. 11, 1994).

Primary Examiner—Terry McKelvey
(74) Attorney, Agent, or Firm—Elias J. Lambiris; Jason I. Garbell

(57) ABSTRACT

The present invention relates to a method for in vivo recombination of homologous DNA sequences. The method is a forced artificial evolution resulting in a DNA sequence encoding a polypeptide having an advantageous property.

32 Claims, 6 Drawing Sheets

Savinase/Savizyn shuffling

| Clone nr. \ Restriction site pos. | 110 | 145 | 155 | 190 | 245 | 280 | 300 | 320 | 340 | 375 | 465 | 590 | 610 | 620 | 670 | 720 | 745 | 775 |
|---|---|---|---|---|---|---|---|---|---|---|---|---|---|---|---|---|---|---|
| 1 | N | N | N | S | S | S | S | S | S | N | N | N | N | N | N | N | N | N |
| 2 | N | N | S | S | N | S | S | N | S | S | S | S | S | S | S | S | S | N |
| 3 | N | N | N | S | S | S | S | S | S | S | N | S | S | S | N | N | S | N |
| 4 | S | S | S | S | S | S | S | S | S | S | S | S | S | S | S | S | S | N |
| 5 | N | N | N | S | S | N | N | S | S | S | S | S | S | S | S | S | N | N |
| 6 | S | S | S | S | S | S | N | S | N | N | N | S | N | N | N | N | N | S |
| 7 | N | N | N | S | S | S | S | S | S | S | N | S | S | S | S | S | S | N |
| 8 | N | N | N | S | S | N | S | N | S | S | N | S | S | S | S | N | N | N |
| 9 | N | N | N | S | S | S | S | S | S | S | S | S | S | S | S | S | N | N |
| 10 | N | N | N | S | S | S | S | S | S | S | S | N | N | N | N | N | N | N |
| 11 | N | N | N | S | S | S | S | S | S | S | N | S | S | S | S | S | S | N |
| 12 | S | S | S | N | N | N | N | N | N | S | S | S | S | S | S | S | S | N |

FIG 6

IN VIVO RECOMBINATION

This is a continuation of International Application PCT/DK97/00567, with an international filing date of Dec. 15, 1997, now abandoned, which claims the benefit of priority of U.S. Provisional Application No. 60/050,590, filed Jun. 24, 1997.

FIELD OF THE INVENTION

The present invention relates to a method for in vivo recombination of homologous DNA sequences. The method is a forced artificial evolution resulting in a DNA sequence encoding a polypeptide having an advantageous property.

BACKGROUND OF THE INVENTION

Homologous recombination between DNA sequences placed on the same plasmid is well known to the skilled artisan (Weber and Weissmann, Nucl. Acid. Res. (1983) 11, 5661–5669). EP 252666 B1 (Novo Nordisk A/S), WO95/22625 A1 (Affymax Technologies N.V.) and WO9101087 discloses in vivo recombination of genes placed on the same plasmid.

EP 449923 B1 (Setratech) discloses a process of intergenic recombination in vivo of partially homologous DNA sequences. The recombination takes place in cells of which the enzymatic mismatch repair system is defective.

J. Biotechnol. (1991) 19, 221–240 discloses a process for inactivating a gene in the genome of B. Amyloliquefaciens. The process involves integration and excision of a pE194 mutant.

In Chemical Abstracts 118:161925 (1993) the minimal sequence length of homology necessary for recombination is determined. The method of determination involves integration of a pE194 derivative carrying a gluconase gene.

In J. Bacteriol. (1982) 152, 524–526 a plasmid pBD9, which comprises the two plasmids from Staphylococcus aureus, pE194 and pUB110, is disclosed. Other plasmids based on pE194 or pUB110 are disclosed in Molecular and General Genetics (1988), 213, 465–70, Molecular and General Genetics (1984), 195, 374–7, Plasmid (1981), 6, 67–77 and Genetika, (1986) 22, 2750–7.

In Yichuan Xuebao (1993), 20, 272–8 (see Chemical Abstracts 120:1670 (1994)), Chen et. Al. disclose the plasmid pNW102, a pE194 derivative, in which the thermostable α-amylase gene from Bacillus licheniformis is inserted. pNW102 was transformed into the Bacillus subtilis strain BF 7658, followed by incubation at non-permissive temperature, allowing homologous recombination between the α-amylase genes of pNW102 and BF 7658. The α-amylase produced of the recombinant strains shows the same characteristics as the α-amylase from Bacillus licheniformis.

However, in the related art there is no indication of that DNA sequences can be recombined in vivo by repeating integration and cross-out in order to obtain a gene encoding a polypeptide with improved characteristics, such as increased stability, improved specificity or higher activity.

Accordingly, a problem of the invention is to provide an improved in vivo process of generating new DNA sequences.

BRIEF DESCRIPTION OF THE INVENTION

The present invention is directed to a in vivo process of generating new DNA sequences. It has turned out that new DNA sequences with improved properties can be generated in a fast and efficient way from at least two homologous DNA sequences by a process involving in vivo exchange of DNA between at least two vectors, each containing a homologous DNA sequence and an origin of replication.

The process of the invention is characterized by, that said exchange of said homologous sequences is done by repeating in vivo at least once, said integration and excision of one vector into the other.

Accordingly, in a first aspect the invention relates to process for in vivo recombination of homologous DNA sequences, comprising the following steps
(a) incubating a cell containing at least two DNA structures, each comprising a DNA sequence and an origin of replication, under conditions which favour integration of one of the DNA-structures into one of the others, thereby forming a hybrid DNA structure;
(b) incubating the cell under conditions which favour crossing out from said hybrid DNA structure, thereby forming novel DNA structures, each comprising a recombined DNA sequence and an origin of replication;
(c) repeating steps a)–b) at least once.

One of the advantages of the in vivo recombination process of the invention is by repeating the exchange in vivo between the DNA sequences it is possible to obtain numerous different recombination patterns between said DNA sequences.

This is illustrated in FIG. 1 herein, which shows the result of in vivo recombination between the two DNA sequences Savinase and Savisyn performed as described in example 1.

In FIG. 1 Savinase/Savisyn recombined clones such as clone no. 3, 8 12 are derived from more than one in vivo recombination event between the two DNA sequences.

BRIEF DESCRIPTION OF THE DRAWING

Further, FIGS. 1 and 2 illustrate a DNA structure system suitable for in vivo measurement of hybrid structure formation, and suitable for performing a forced cross out of the DNA hybrid structure.

FIG. 1:
DNA structure pTS:
Suitable active promoter directing expression of active protein
$Erm^R$: antibiotic resistance gene
DNA structure pTR comprises:
Not any active promoter to direct transcription of GFP
GFP: Green Fluorescent Protein
The $Erm^R$ antibiotic resistance gene in pTS is active due to the active promoter.
The GFP gene in pTR is inactive (i.e. the gene is non-transcribed) due to there is not an active promoter to drive expression of the gene.

FIG. 2: After formation of the hybrid structure according to the invention GFP is now active (driven by the promoter). This makes it possible to in vivo measure the hybrid structure formation (see below for further details).

In contrary the $Erm^R$ antibiotic resistance gene is now inactive (i.e. the gene is non-transcribed) due to there is not an active promoter to drive expression of the gene. Forced cross out of the DNA hybrid structure is performed by incubating the cells under $Erm^R$ antibiotic pressure, thereby forcing a cross out of the DNA hybrid structure, since the cell is only able to express the $Erm^R$ antibiotic resistance gene after the crossing out of the DNA structure has taken place.

Figure 4:
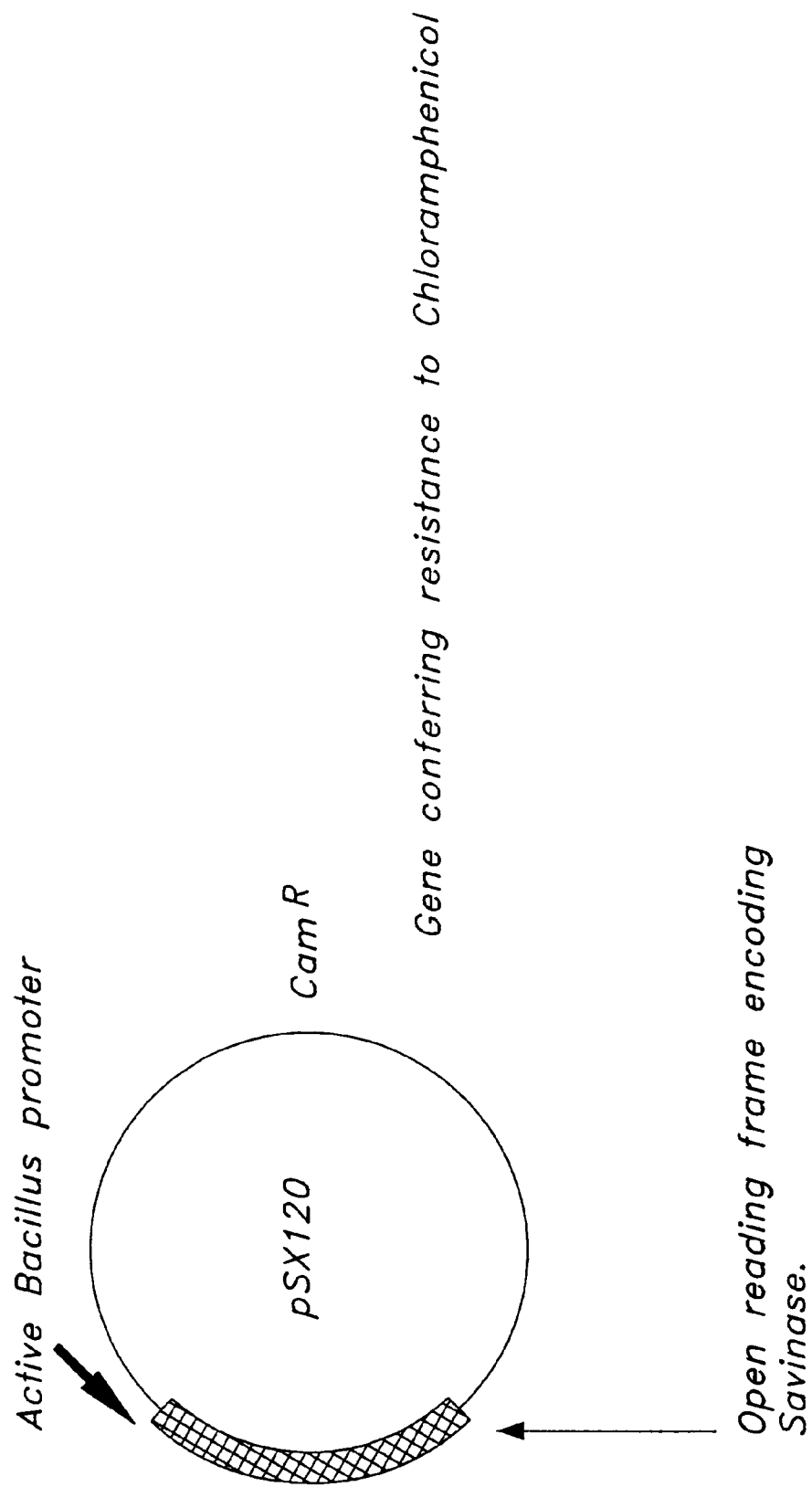
Figure 5:
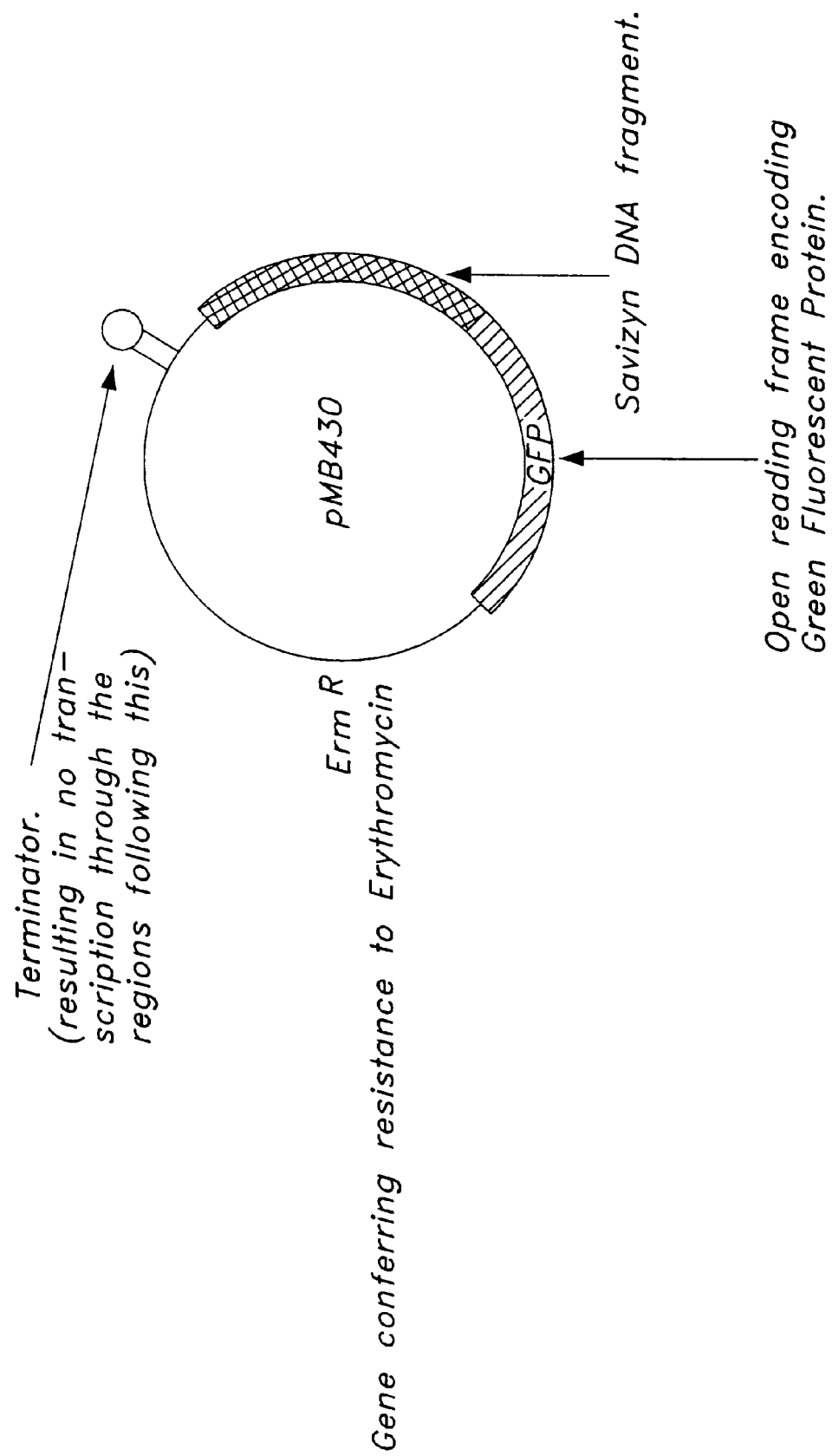

FIGS. 4 and 5: Illustrate the two vectors pSX120 (FIG. 4) and pMB430 (FIG. 5) used as described in example 1 to in vivo recombine the two DNA sequences Savinase and Savisyn.

pSX120 comprises i) an open reading frame encoding Savinase, ii) an active promoter directing transcription of Savinase, and iii) a gene conferring resistance to chloramphenicol ($Cam^R$).

pMB430 comprises i) a Savizyn DNA fragment, ii) a terminator (resulting in no transcription through the regions following this), iii) a gene conferring resistance to erythromycin ($Erm^R$), and iv) an open reading frame encoding Green Fluorescent Protein (GFP).

FIG. 6: Illustrates the results of Savinase/Savisyn in vivo recombination performed as described in example 1.

The schematic representation shows 12 of the shuffled/recombined clones.

Horizontally are given the positions of the restriction sites unique for Savizyn.

The letter "S" denotes that the sequence at this position is identical to the Savinase sequence and the letter "Z" denotes that the sequence stems from Savizyn. All of the sequenced clones are different in their pattern of recombination.

Definitions

As used herein, the following terms have the following meanings:

The term "DNA sequence" includes any DNA sequence which is desirable to modify according to the invention e.g. a DNA sequence encoding, a polypeptide, for example an enzyme, pharmaceutically active polypeptides, e.g. insulin growth hormone human hormones or growth regulators, and sequences such as promoters, transcription or translation regulators and other intracellular polynucleotides and polypeptides.

The term "homologous" means the DNA sequences have some stretches of identical nucleotides, allowing recombination in vivo. Said stretches within the DNA sequences are at least 15 base pair long, more preferably at least 25 base pair long, even more preferably at least 50 base long, and most preferably at least 150 base pair or more.

The term "homologous" comprises stretches of DNA sequences that are from 60% identical to DNA sequences that differs in only one nucleotide. It is preferred that the stretches of DNA sequences are more than 70% identical, more preferably at least 80%, especially more than 90% identical, and more preferred that the stretches of DNA sequences are 95% identical, most preferred at least 97%.

Within the stretches of the DNA sequences of interest, the DNA sequence homology referred to above is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the homologous DNA sequences of interest exhibits a degree of identity preferably as described above.

The term "Recombined DNA sequence" means the DNA sequence which is a result of a recombination event between at least two DNA sequences. The recombination event may be a single recombination event or may be first a recombination event between at least two DNA sequences followed by a cross out at a different site than the first recombination event.

The term "DNA structure" means a DNA molecule, e.g. a vector, a plasmid, a chromosome (e.g. a *Bacillus subtilis* chromosome), a virus, a phage, a transposon or a genome.

The term "vector" means any linear or circular DNA molecule that is able to contain a DNA sequence to be recombined and an origin of replication. The term includes any vector known to the skilled artisan e.g. a plasmid or a phage. The DNA sequence is optionally—but not necessarily—under control of a promoter.

The term "a cell" used herein in connection with a in vivo recombination process of the invention is intended to cover both "a cell" and "a cell population".

The term "transferring" means that the DNA structure is introduced into a cell. The DNA structure may be introduced using techniques known in the art for direct introduction of DNA, e.g. by use of electroporation, transformation of competent cells, protoplast transformation, transfection, transduction, conjugation or ballistic transformation.

The term "incubating" (or cultivating, growing) means that the cell is treated in such a way that the normal cell functions are active, especially the functions necessary for recombination. The cell can be incubated on a solid substrate (agar petri disc) or the cell can be incubated under submerse conditions. It is preferred that the cell is incubated in a test tube, e.g. an eppendorph test tube. In the case of a temperature-sensitive origin of replication, the test tube is conveniently placed in an automatic termocycler. Further the cell may be incubated in standard shake-flaks.

The term "origin of replication" (ori) means a region where replication of a DNA structure is initiated. The term functional in connection with origin of replication means that replication can be initiated from the origin. The term non-functional means that no replication is initiated under the given conditions, or that the initiation of replication is reduced, e.g. to a level insufficient for survival of a cell containing a DNA structure with a marker gene and the ori, under appropriate selection pressure.

The term "temperature sensitive" in connection with origin of replication or vector means the vector is unable to replicate at e.g. increased temperatures, i.e. non-permissive conditions, which yet permit growth of the parent cell.

The term "temperature resistant" in connection with origin of replication or vector means the vector is able to replicate at increased temperatures.

The term "DNA library" is a library comprising numerous different DNA sequences. A DNA library may be made according to standard procedures known in the art, such as e.g. by in vitro DNA shuffling/DNA recombination (WO 95/17413, WO 95/22625) and/or Error-prone PCR and cassette mutagenesis.

A DNA library herein may comprise as low as 2–20 different sequences, as e.g. a library where only one amino acid is varied. Further a DNA library may comprise numerous different DNA sequences, e.g. up to $10^{10}$ different sequences.

DETAILED DESCRIPTION OF THE INVENTION

The present invention comprises a process for in vivo recombination of homologous DNA sequences, comprising the steps (a) incubating a cell containing at least two DNA structures, each comprising a DNA sequence and an origin of replication, under conditions where i) at least one origin of replication is non-functional and ii) the cell is under a selective pressure which only allows growth of the cell if it contains the DNA structure which is having the non-functional origin (i.e. favouring an integration of one of the DNA-structures into one of the others, thereby forming a hybrid DNA structure);

(b) changing of said conditions to conditions, where fewer origins of replication are non-functional than in step a) (i.e. favouring a crossing out from said hybrid DNA structure);

(c) repeating steps a)–b) at least once.

The recombined DNA sequence will encode new polypeptides having new properties. It is then possible to incorporate a selection or screening system in the process of the invention in order to select and/or screen for desired properties encoded by of or more of the recombined DNA sequence(s).

The number of repetition(s) in step (c) above may be one repetition or it may be more such as 5–10 repetitions or 50–100 or even higher numbers of repetitions.

It is preferred that integration is forced (or made favorable for survival of the DNA structure) by incubation of the cell under such conditions where the origin of replication of a DNA structure is non-functional, and that cross out is forced by incubation of the cell under such conditions where the origin of replication of a DNA structure again is functional.

In another preferred embodiment the routine depicted above in the steps (a) to (c) it is preferred that the cells are kept under constant conditions (e.g. constant temperature and selection pressure) where spontaneous cross-in and cross-out happens. That is the shuffling procedure in the cells is repeated without changing the conditions repeatedly.

In a number of DNA structures, such as in many Bacillus DNA structures (vectors) (*Bacillus subtilis* and Other Gram-Positive Bacteria, Sonensheim et al., 1993, American Society for Microbiology, Washington D.C.) the origin of replication comprise prise a ori(+) and a ori (−). ori(+) controls where replication of the first DNA strand starts, and ori(−) controls the initiation point for replication on the second strand (*Bacillus subtilis* and Other Gram-Positive Bacteria, Sonensheim et al., 1993, American Society for Microbiology, Washington D.C.).

In an embodiment of the process of the invention, at least one DNA structure does not comprise ori(−) (i.e. only comprise ori(+)). Preferably the DNA structure which does not comprise ori(−) is a DNA structure which origin (i.e. herein ori(+)) is functional during the hybrid DNA structure formation performed according to the invention.

One advantage of this embodiment of the invention is when only ori(+) is functional in said DNA structure, this DNA structure is in a single-stranded state for relatively longer period, compared to a DNA structure comprising both ori(+) and ori(−). This prolonged single-stranded state facilitate the hybrid DNA structure formation according to a process of the invention.

Preferably, the DNA structure which does not comprise ori(−) as described above is a Bacillus structure, more preferred a Bacillus vector.

Figure 1:
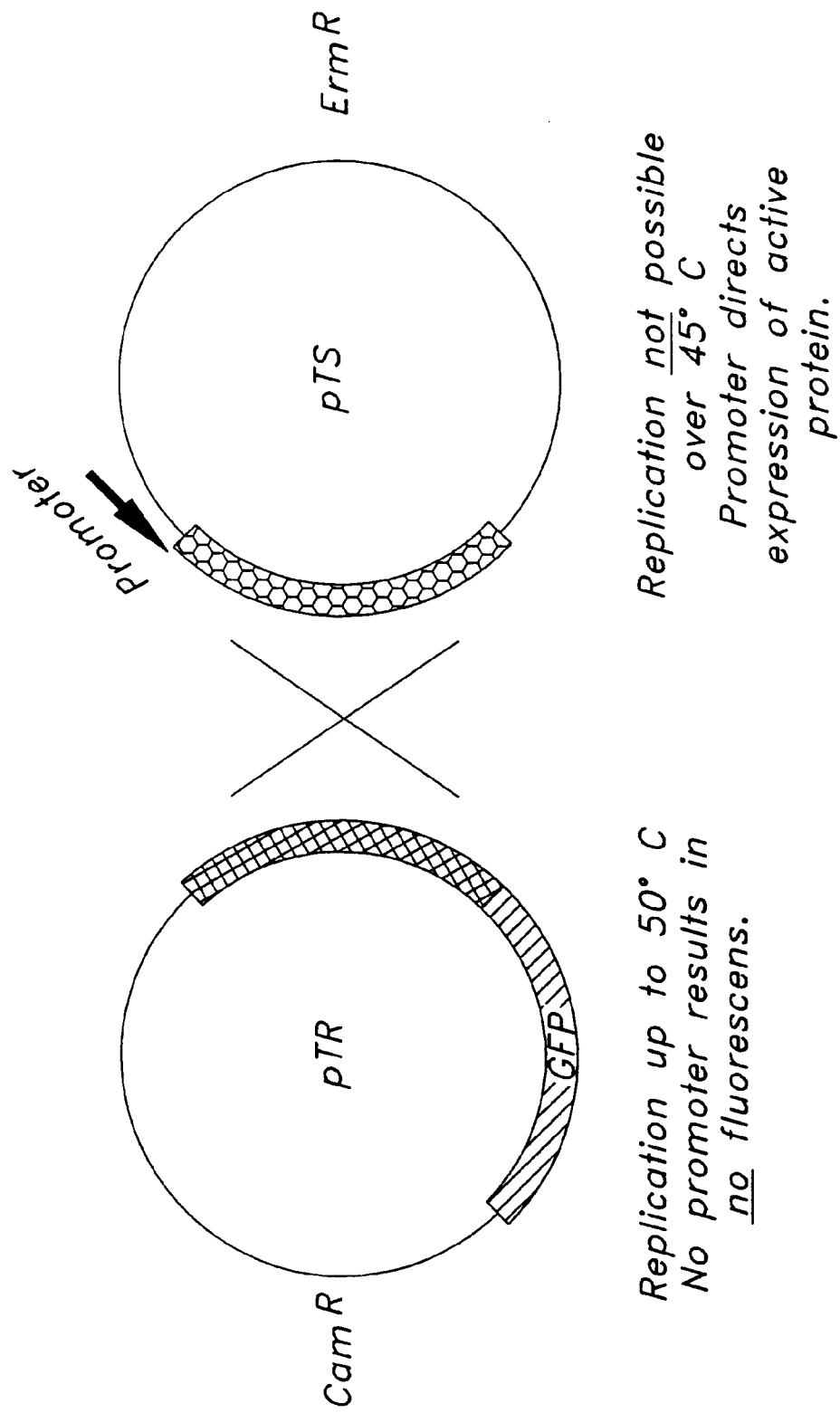
FIG. 1 illustrates the recombination of two DNA sequences, placed on the plasmids pTR, temperature resistant since origin of replication is functional at 50° C., and pTS, temperature sensitive since origin of replication not functional over 45° C. Under non-permissive conditions (i.e. at 50° C.), pTS integrates into pTR, forming a hybrid plasmid.

In order to illustrate this concept, an example is a modified pTR (TR: temperature resistence) Bacillus vector which does not comprise ori(−) (see FIG. 1). If the hybrid formation is performed at 50° C. only the origin of pTR is functional (origin of pTS (TS: temperature sensitive) is not functional) (see FIGS. 1,2). The DNA structure pTR only comprise ori(+) and is therefore in a single-stranded state for relatively longer period, which facilitate the recombination event and consequently hybrid formation with the pTS DNA structure (see FIGS. 1,2).

It is more preferred that one DNA structure is a vector which is able to replicate under certain (permissive) conditions and unable to replicate under other (non-permissive) conditions. The vector may, for instance, be one which is temperature-sensitive for replication. Thus, the vector may be one which is unable to replicate at increased temperatures, which yet permit growth of the parent cell. The cell is initially incubated at a temperature permitting vector replication and subsequently after integration into the other DNA structure may have taken place, incubated at a temperature which does not permit vector replication so that the vector is lost from the cells unless integrated.

The vector may further comprise a selectable marker. In this case, the incubation at the non-permissive temperature may be conducted under selective conditions to ensure that only cells containing the integrated vector (which includes the DNA sequence and the selectable marker), will survive.

Further, it is preferred to construct a system where it is possible in vivo to measure formation of the hybrid structure.

Preferably, this is done by constructing a system wherein an in vivo screenable or selectable protein is expressed only after the hybrid structure has been formed.

Preferably, said screenable protein is a protein which is fluorescent under suitable exposure, and in particular said fluorescent protein is Green Florescent protein (GFP) or variants thereof.

Green Florescent protein (GFP) or variants thereof and how the GFP's are activated to fluoresce are described in the art and reference is made to (Crameri et al. Nature Biotechnology 14:315–319 (1996); and Cormack et al. GENE 173:33–38 (1996)) for further details.

One of the advantages of using such a screenable protein which is fluorescent under suitable exposure of light, and in particular GFP or variants thereof, is that it is then possible by e.g. fluorescent-activated cell sorting (FACS) technology to selectively sort out cells which comprise said hybrid structure. This may eliminate background of cells, which do not comprise said hybrid structure after performing of step a) according to the first aspect of the invention.

FACS is a widely known screening technology and reference is made to (Cormack et al. "FACS-optimized mutants of the green fluorescent protein (GFP)" GENE 173:33–38 (1996)) for further details.

Figure 2:
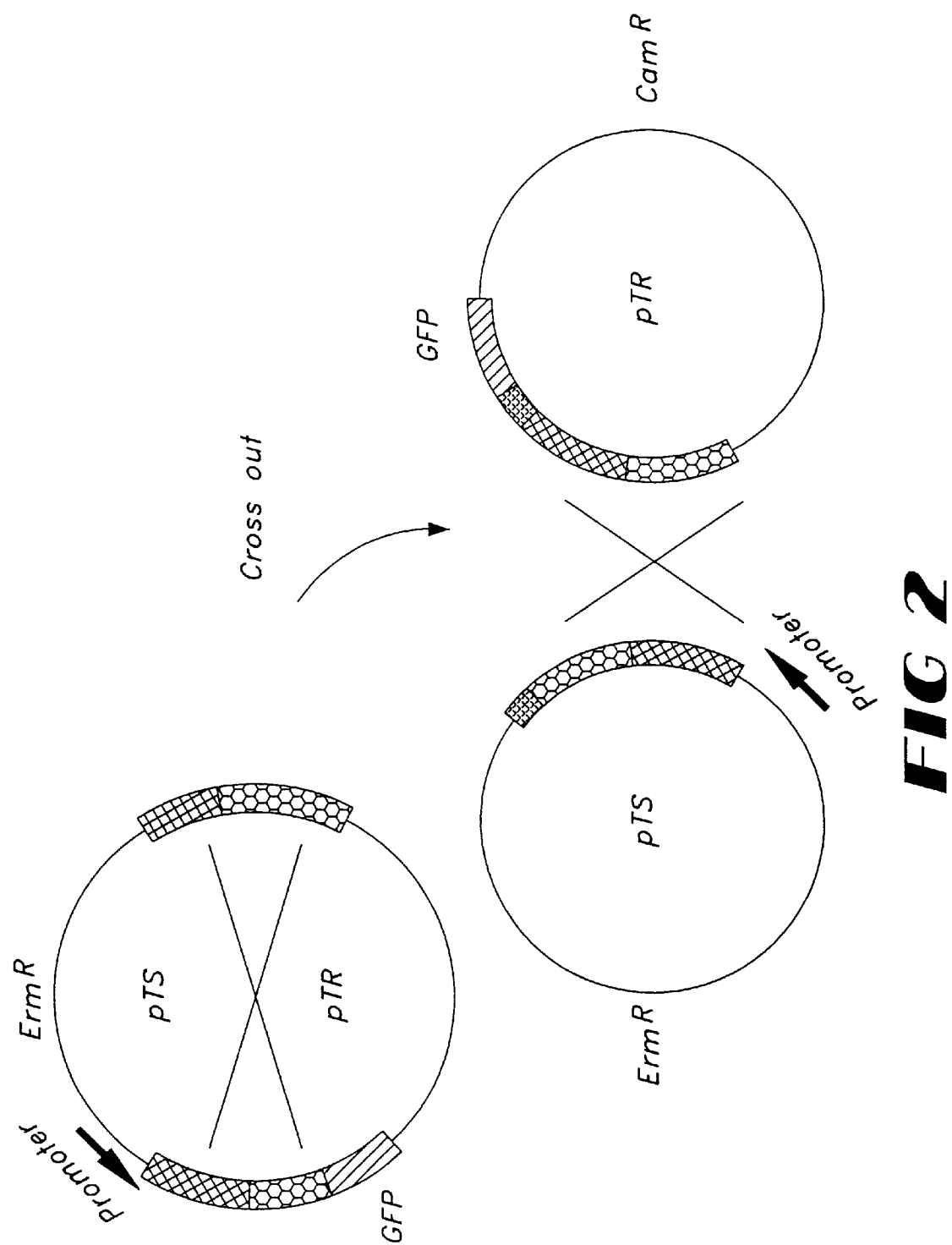
FIG. 2 illustrates the cross out from the hybrid plasmid, forming two new DNA sequences, each placed on a plasmid. Repeated crossing in and out may be done by e.g. temperature cycling or simply by keeping temperature pressure and selecting for resistance of pTS (i.e. $Erm^R$).
Figure 3:
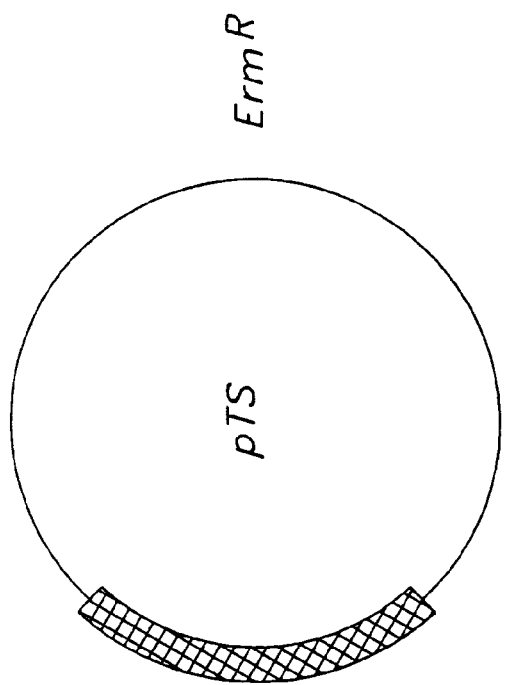
FIG. 3 illustrates the plasmids which are obtained after repeated integration and crossing out events.
Figure 3:
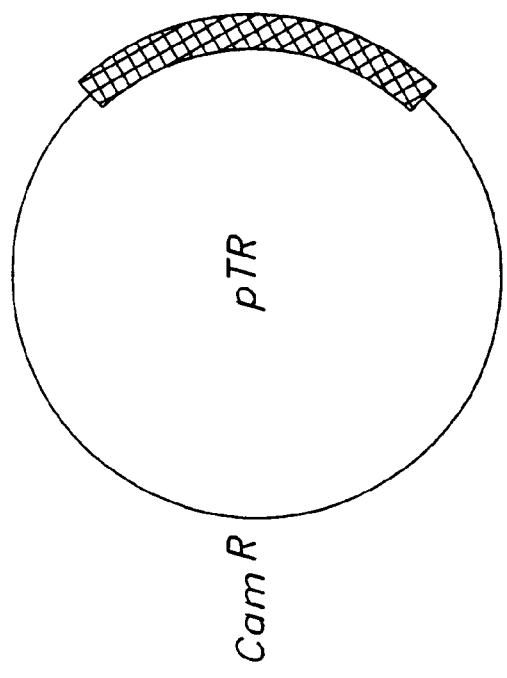

In order to illustrate a suitable system enabling in vivo measurement of the formation of the hybrid structure, an example of a suitable system is shown in FIGS. 1 and 2.

Alternatively to the use of a screenable protein as discussed above, it may be advantageously to use a selectable marker, wherein said selectable marker is only transcriptionally active when the hybrid structure is formed.

Further, it is preferred to that the crossing out from the hybrid DNA structure, in step b) of the first aspect of the invention, is a forced crossing out event.

Forced crossing out from the hybrid structure may be performed by:

i) constructing a system wherein the DNA hybrid structure does not express a selectable marker, and at least one of the at least two DNA structures in step a) of first aspect is able to express said selectable marker;

ii) incubating the cell under selectable conditions, thereby forcing a cross out of the DNA hybrid structure, since the cell is only able to express the marker gene after the crossing out of the DNA hybrid structure has taken place.

Preferably, selectable marker gene mentioned above is expressed on a DNA structure where the origin of replication is non-functional during a forced integration of the DNA structures into a DNA hybrid structure performed as described above, and preferably the selectable marker gene is an antibiotic resistance gene. See below for further description of suitable selectable marker genes.

In order to illustrate the concept of forced crossing out from the hybrid DNA structure, an example of a suitable system is shown in FIGS. 1 and 2.

The selectable marker may be any marker known in the art, for instance a gene coding for a product which confers antibiotic resistance to the cell, which confers prototrophy to an auxotrophic strain, or which complements a defect of the host, (e.g. dal genes introduced in a dal—strain; cf. B. Diderichsen (1986), Bacillus: Molecular Genetics and Biotechnology Applications, A. T. Ganesan and J. A. Hoch, Eds., Academic Press, pp. 35–46. The selectable marker may, e.g., be excised from a known source or present on a vector, e.g. a plasmid, used for the construction of the DNA structure to be used in the method of the invention.

This selection may be accomplished by growing the cells under selection pressure for the selection marker encoded by the marker gene.

The DNA structure (in which the vector is to be integrated) may contain a gene encoding any selectable marker, e.g. of any type as described above in connection with the marker optionally carried by the vector to be used in the method of the invention. Thus, the marker gene may encode an antibiotic resistance such as resistance to kanamycin, tetracycline ampicillin, erythromycin, chloramphenicol, or a resistance to various heavy metals such as selenate, antimony or arsenate.

In a preferred embodiment, the cell used in the process is defective or transitorily inactivated in the enzymatic mismatch repair system or has a reduced level of mismatch repair. In the synthesis of DNA, errors can occur and the resulting non-complementary pairs of bases are called mismatches. A process for the correction of errors (mismatches) in DNA exists. In *E. coli* the errors are very rapidly and accurately detected by two enzymes (MutS and MutL) enabling a third enzyme (MutU) to unwind the two DNA strands and a fourth enzyme (MutH) to cut the neosynthesized strand on a sequence of DNA (GATC) itself methylated later. For a closer explanation, reference is made to EP 449923 (Setratech), the contents of which hereby are incorporated by reference.

In another preferred embodiment the cell used in the process is impaired or hampered in the major recombination enzymes such as AddAB. It has been shown that a strain impaired in the AddAB genes shows a higher frequency of homologous recombination. Both legitimate and illegitimate recombination frequency are increased. But especially the recombination frequency for illegitimate recombination is favoured when working with a strain impaired or hampered in the AddAB ATP-dependent nuclease (Meima, R ; Haijema, B J; Dijkstra, H; Haan, G J; Venema, G; Bron, S (1997) Role of enzymes of homologous recombination in illegitimate plasmid recombination in *Bacillus-subtilis*. JOURNAL OF BACTERIOLOGY Vol. 179, No. 4 pp. 1219–1229.)

In another preferred embodiment the cell used in the process is over-expressing one of the key recombination enzymes, recA. The recA enzyme is involved in homologous recombination by promoting renaturation of ssDNA to form the heteroduplex molecules necessary for the recombination event and initiates the exchange of DNA strands. (PROGRESS IN NUCLEIC ACID RESEARCH AND MOLECULAR BIOLOGY Vol. 56, pp. 129–223 (1997)). The recA over-expression can be achieved by either classical mutagenesis of the host strain or cloning of a highly expressed recA gene.

In another preferred embodiment the cell used in the process is subjected to UV, X-ray or DNA damaging agents to increase recombination frequency between the two homologous genes to be shuffled. Stress like UV, X-ray or DNA damaging agents is known to induce the recombination enzymes via the SOS response and activate enzymes involved in recombination processes like recA. (BACILLUS SUBTILIS AND OTHER GRAM-POSITIVE BACTERIA, pp.529–537 (1993)).

In another preferred embodiment the pTR based plasmid used as a carrier of one of the genes to be shuffled is replaced by either a low-copy version of pTR or another *B. subtilis* compatible low-copy plasmid like pWV01, (MOLECULAR AND GENERAL GENETICS Vol. 249, No. 1 pp. 43–50 (1995)), pTA1060, (JOURNAL OF BACTERIOLOGY Vol. 142, No. 1 pp. 315–8 (1980)) or pAMb1, (JOURNAL OF BACTERIOLOGY Vol. 157, No. 2 pp. 445–53 (1984)).

In a further preferred embodiment the one of DNA construct comprising one the genes to be shuffled is situated on the chromosome of the cell and another DNA construct, comprising another gene of interest to be recombined is a plasmid. When performing an in vivo recombination process of the invention the plasmid will be recombined with the DNA construct on the chromosome. Said plasmid may e.g. be a temperature sensitive plasmid.

The advantages of using a low-copy pTR, or a system where one of the DNA constructs is situated on the chromosome as described above, is that the hybrid DNA construct after recombination of the two homologous genes will be the predominant form of the genes in the cell. A high-copy background of non-recombined pTR plasmids will inevitably reverse the gene hybrids formed in the first round back to wildtype after the second round of recombination and therefore prohibit any shuffling of the two genes. When using the chromosome as a carrier of one of the genes no wildtype background can coexist when the pTS has integrated via the homologous genes.

It is preferred that the cell used in the process is a cell suitable for large scale production of the product of the recombined DNA sequence. It is preferred that the cell is a bacterial cell, more preferred a Bacillus cell, most preferred a *Bacillus subtilis* cell.

The DNA sequences to be recombined may be isolated/cloned from organisms containing the sequences in a manner known per se. For instance, a suitable oligonucleotide probe may be prepared on the basis of a first DNA sequence of interest in order to obtain a second DNA sequence homologous to the first sequence. Alternatively, the DNA sequence can be amplified by PCR based on primers designed according to knowledge of conserved regions.

I different embodiments of the present content is used the term "a set of homologous DNA sequences ("set A" "set B", "setC" etc.)", e.g. in relation to an embodiment of the invention relating to a process according to the invention, wherein the homologous DNA sequences are comprised of two or more different set of homologous DNA sequences ("set A" "set B", "setC" etc.), and wherein each of said set of homologous sequences ("set A" "set B", "setC" etc.) are inserted in a different DNA construct ("DNA construct A", "DNA construct B", "DNA construct C" etc.) according to the invention.

This term is used to illustrate that an in vivo recombination process of the present invention may be used to recombine numerous "sets" of homologous DNA sequences. Each individual "set" of homologous DNA sequence(s) may individually comprise from only one to numerous (e.g. a "set" comprising a DNA library) individual homologous DNA sequence(s).

Each of said "sets" of homologous DNA sequences ("set A" "set B", "setC" etc.) may then be inserted in a different DNA construct ("DNA construct A", "DNA construct B", "DNA construct C" etc.) according to the invention. Each of said different DNA construct are preferably different on important parameters, according to the invention, such as different origin of replication, different selectable markers etc.

All of said DNA constructs ("DNA construct A", "DNA construct B", "DNA construct C" etc.) may then be transferred into a cell, according to the invention, and when performing a process for in vivo recombination of the invention, then each of the individual DNA constructs ("DNA construct A", "DNA construct B", "DNA construct C" etc.) may then recombine randomly according to the invention. After a few repetitions of a process, of the invention, this will give a DNA population, in the cell population, comprising numerous different combinations of different recombined DNA sequences, recombined randomly between all "sets" of homologous DNA sequences used in the process.

Further, the term "a set of homologous DNA sequences ("set A" "set B", "setC" etc.)" is used herein to illustrate one of the advantages of an in vivo recombination process of the invention, which is the flexibility of the system to recombine both set of homologous DNA sequences comprising one, few and/or numerous (e.g. big DNA libraries) of individual homologous DNA sequences.

Accordingly, an embodiment of the invention relates to process according to the invention, wherein said sets of homologous DNA sequences each only contain one DNA sequence (i.e. recombination of two or more homologous sequences).

Further in embodiments of the invention the homologous DNA sequences to be recombined are derived from a pre-made DNA library and/or derived from individually different pre-made libraries.

Homologous DNA derived from such DNA libraries are inserted into a vector according to the invention (i.e. DNA representing the DNA library is ligated (inserted) into a vector). As described herein the process of the invention comprise at least two DNA structures (e.g. vectors), which are different in a way which allow forced in vivo recombination of said vectors.

Homologous DNA representing DNA libraries may be inserted into only one and/or both of said different vectors.

I.e. if for instance homologous DNA representing one DNA library is inserted (ligated) into one of said different vectors and homologous DNA representing another DNA library is inserted into the other vector this will allow fast and efficient recombination between two different libraries by an in vivo recombination process according to the invention. To illustrate this concept, DNA representing one library may be inserted into a pTR vector (see FIG. 1) and DNA representing another library may be inserted into a pTS vector (see FIG. 1). Just a few repeating in vivo recombination events performed by a process according to the invention will then give a cell population representing a new library which is a combination of the two libraries mentioned above.

Accordingly, embodiments of the invention relates to a process according to the invention, wherein at least one of the sets of homologous DNA sequences is derived from a pre-made DNA library, and at least one of said sets of homologous DNA sequences is a DNA sequence which is homologous to said DNA library (i.e. resulting in a process for in vivo recombination of said DNA library to a DNA sequence which are homologous to said DNA library); or a process according to the invention, wherein the sets of homologous DNA sequences is derived from the same pre-made DNA library (i.e. resulting in a process for in vivo recombination of said DNA library); or a process according to the invention, wherein the sets of homologous DNA sequences are derived from at least two different pre-made DNA libraries (i.e. resulting in a process for in vivo recombination of at least two different DNA libraries).

In order to obtain even further recombination between the DNA sequences it may be preferred to perform an isolation of the DNA structures after a first round of in vivo recombination of said DNA sequences performed according to the invention. Said isolated structures are then re-transformed into the cells and a further process round of in vivo recombination is then performed.

The advantages of this step is illustrated by following example:

Set A is a vector A wherein DNA sequences a, b are introduced individually in said vector A (i.e. the vector A population comprises a vector with DNA sequence a, and a vector with sequence b); and Set B is a vector B wherein DNA sequences c, d are introduced individually in said vector B (i.e. the vector B population comprises a vector with DNA sequence c, and a vector with sequence d).

Vector A and B are then transformed into a cell population and in vivo recombined according to the invention. This will give recombination between DNA sequences ac, ad, bc, bd. The vectors A, and B comprising said recombined sequences is isolated, and re-transformed into said cell population. In vivo recombination according to the invention will then give all possible recombination of said four (a,b,c,d) DNA sequences, such as recombination of abc, abdc, etc.

In even further embodiments the invention relates to a process according to the invention, wherein two sets of homologous DNA sequences ("set A" and "set B") are recombined in vivo, comprising the steps a) inserting sequence(s) from "set A" in a vector containing a temperature resistant origin of replication and a gene for a first marker;

b) inserting sequence(s) from "set B" in a vector containing a temperature sensitive origin of replication and a gene for a second marker;

c) transferring the vectors into a cell;

d) Incubating the cell at a temperature where both origins of replication are functional, optionally under a selection pressure that favours cells with both marker genes;

e) shifting the temperature to a temperature, where only the temperature resistant origin of replication is functional;

f) repeating steps d)–e) at least once; or a process according to the invention, wherein two sets of homologous DNA sequences ("set A" and "set B") are recombined in vivo, comprising the steps
a) inserting sequence(s) from "set A" in a vector containing a temperature resistant origin of replication and a gene for a first marker;
b) inserting sequence(s) from "set B" in a vector containing a temperature sensitive origin of replication and a gene for a second marker;
c) transferring the vectors into a cell;
d) Incubating the cell at a temperature where only the temperature resistant origin of replication is functional, optionally under a selection pressure that favours cells with both marker genes;
e) optionally, shifting the temperature to a temperature, where both origins of replication are functional;
f) repeating steps d)–e) at least once.

In a further aspect the invention relates to a method for producing one or more recombinant protein(s) having a desired biological activity comprising:
a) performing a process for in vivo recombination of homologous DNA sequences (the process is performed according to the invention as described herein), wherein at least one of the DNA structure(s) is an expression vector;
b) expressing the numerous different recombinant polypeptides encoded by the numerous different recombined DNA sequences from step a); and
c) screen or select the numerous different recombinant proteins from step b) in a suitable screening or selection system for one or more recombinant polypeptides(s) having a desired activity.

Preferably, the expression vector in step a) above is a DNA structure which is unable to replicate (e.g. having a non-functional origin of replication) during a forced hybrid DNA structure formation (i.e. integration of said structures into each other) performed according to a process for in vivo recombination of homologous DNA sequences according to the invention. This will improve the probability that the expression vector, after a crossing-out event of said hybrid-structure according to the invention, comprise recombined homologous DNA, since the only way said expression vector may have survived the process of forced hybrid formation is by actually recombine with another DNA structure, which is able to replicate under the conditions used to force said hybrid-structure formation.

After the process for in vivo recombination have been performed (step a) above), and before the expression and screening steps b) and c) above, it may be advantageously to make a cell population mainly comprising only the expression vector (i.e. other DNA construct(s) are partly or nearly completely removed from the cell population). This is particular advantageously when the expression vector is unable to replicate during the forced hybrid DNA structure formation as described immediately above, since such a cell population will have a very limited background of non-recombined DNA sequences of interest, which is advantageously in the subsequent screening step (step c) above).

Making a cell population mainly comprising only the expression vector may be performed according to standard procedures known in the art, such as growing the cell population at conditions selectively favouring replication of the expression vector, as compared to the other DNA structures; or selectively purify said expression vector form the cells and subsequently transfer this into a new cell population.

Expression the recombinant polypeptides encoded by the recombined sequence in step a) above may be performed by use of standard expression vectors, and/or a standard expression vector may be modified in order to comprise elements specially suitable for a in vivo recombination process according to the invention.

A suitable screening or selection system, to screen or select the numerous different recombinant proteins from step b) above, will depend on the desired biological activity.

A number of suitable screening or selection systems to screen or select for a desired biological activity are described in the art. Examples are:

Strauberg et al. (Biotechnology 13: 669–673 (1995), which describe a screening system to screen for Subtilisin variants having a Calcium-independent stability;

Bryan et al. (Proteins 1:326–334 (1986)), which describe a screening assay to screen for Protease having a enhanced thermal stability; and PCT-DK96/00322 which describe a screening assay to screen for lipases which are having an improved wash performance in washing detergents.

A preferred embodiment of the invention comprise screening or selection of recombinant protein(s), wherein the desired biological activity is improved performance in dish-washing or laundry detergents. Examples of suitable dish-wash or laundry detergent are disclosed in PCT/DK96/00322 and WO 95/30011.

The invention also comprises a set (at least two) of vectors, comprising at least two different origins of replication able to function in the same cell under permissive conditions, and at least two homologous DNA sequences encoding polypeptides. In a preferred embodiment, at least one origin of replication is temperature sensitive. The vector may preferable be a plasmid.

The invention further comprises a vector system, comprising at least
a) a vector A containing a DNA sequence encoding a polypeptide and an origin of replication, and
b) a vector B containing a DNA sequence homologous to the DNA sequence in vector A, and an origin of replication that differs from the origin of replication in vector A. The vectors may preferable be plasmids.

It is preferred that the DNA sequence encodes polypeptides with a biological activity, especially enzymes and in particular enzymes such as an amylase, lipase, cutinase, cellulase, oxidase, phytase, and a protease.

The invention further comprises a new, recombined DNA sequence, characterised in that has be produced by a process according to the invention, or it is encoding a recombinant protein having a desired biological activity, wherein said recombinant protein having a desired biological is produced by the method according to method for producing one or more recombinant protein(s) having a desired biological activity according to the invention.

The invention further comprises a process for producing a polypeptide, especially an enzyme, comprising i) growing a cell expressing a polypeptide encoded by a recombined DNA sequence according to claim 38, and ii) purifying said expressed polypeptide.

The invention further comprises a new polypeptide, especially an enzyme, characterised in that it is produced by a process according to the invention.

The invention further comprises a polypeptide, especially an enzyme, characterised in that it is encoded of a recombined DNA sequence according to the invention.

Polypeptides of the present invention include peptides and proteins, and optionally glycosylated forms thereof.

Examples are enzymes, pharmaceutically active polypeptides such as analogues of human or mammal polypeptides, e.g. insulin, growth hormone, human hormones or growth regulators.

The invention is described in further detail in the following examples which are not in any way intended to limit the scope of the invention.

EXAMPLES

Materials and Methods

Strains

*E.coli:* SJ2 (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis.* J. Bacteriol., 172, 4315–4321) Electrocompetent cells prepared and transformed using a Bio-Rad GenePulser™ as recommended by the manufacturer.

*B.subtilis* DN1885 Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis.* J. Bacteriol., 172, 4315–4321). Competent cells were prepared and transformed as described by Yasbin, R. E., Wilson, G. A. and Young, F. E. (1975) Transformation and transfection in lysogenic strains of *Bacillus subtilis:* evidence for selective induction of prophage in competent cells. J. Bacteriol, 121:296–304.

*B.subtilis* PL1801. This strain is the *B.subtilis* DN1885 with disrupted apr and npr genes (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis.* J. Bacteriol., 172, 4315–4321).

Plasmids pSX120: *B. subtilis* expression vector (Described in EP 405901, and WO 91/00345). This vector comprise the wild-type Savinase gene.

pE194: (Horinouchi, S and Weisblum, B., 1982, J. Bacteriol. 150:804–814).

pSX222: *B. subtilis* expression vector (Described in WO 96/34946, and WO 92/19729). This vector comprise the synthetic Savinase gene herein called Savisyn. In the Savisyn gene is introduced a large number of restriction sites as compared to the wild-type Savinase gene comprised in pSX120.

pUC19: Yanisch-Perron, C., Vieria, J. and Messing, J. (1985) *Gene* 33, 103–119.

pF64L-S65T-GFP: is the *E.coli* plasmid encoding the DNA fragment encoding the F64L-S65T-GFP described in WO 97/11094.

pMUTIN-4-MCS: Plasmid can be obtained from Laboratoire de Genetique Microbienne, Institut National de la Recherche Agronomique, 78352 Jouy en Josas—CEDEX, France.

Solutions/Media

TY and LB agar (as described in Ausubel, F. M. et al. (eds.) "Current protocols in Molecular Biology". John Wiley and Sons, 1995).

LBPG is LB agar supplemented with 0.5% Glucose and 0.05 M potassium phosphate, pH 7.0

LBPGSK plates are LBPG media with agar and 1% of skimmed milk.

Antibiotics are used in different medias in concentrations of 6 µg/ml Chloramphenicol, 10 µg/ml Kanamycine and 5 µg/ml og Erythromycine.

TE-buffer (as described in Ausubel, F. M. et al. (eds.) "Current protocols in Molecular Biology". John Wiley and Sons, 1995).

General Molecular Biology Methods

DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restriction endonucleases, ligases, polymerases, PCR polymerases etc., are obtained from New England Biolabs, Inc.

Construction of the Temperature Sensitive Shuffling Plasmid pMB430 was constructed in a five step cloning process as depitched in the following, the entire DNA sequence is found in SEQ ID No. 1.

1)

The temperature sensitive plasmid pE194 was modified by introducing multiple cloning sites around the unique ClaI site of the pE194 plasmid and thus destroying the ClaI site. This introduction was done by PCR using the primers #22899 and #24039 to amplify the whole plasmid and introducing several unique cloning sites.

The PCR was performed as follows:

1 µl of pE194 Qiaquick plasmid prep was used for 50 µl PCR amplification in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer:

22899 5'-GCAGCTGGATCCGCGGCCGCGAATTCGTC TTTTGCGCAGTCGGC-3' (SEQ ID NO:2)

24039
5'-GCAGCTGGATCCGGGCCCGGGAAGCTTCGA TTCACAAAAAATAGGCACACG-3' (SEQ ID NO:3)

The PCR reactions were performed using a DNA thermal cycler (Landgraf, Germany). One incubation at 94° C. for 1 min followed by forty cycles of PCR performed using a cycle profile of denaturation at 94° C. for 1 min, annealing at 55° C. for 1 min, and extension at 72° C. for 2 min. Five-µl aliquots of the amplification product was analyzed by electrophoresis in 0.7% agarose gels (NuSieve, FMC).

Subcloning of PCR Fragment

Forty-five-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. Fifty-µl of the purified PCR fragment was digested with BamHI, electrophoresed in 0.8% low gelling temperature agarose (SeaPlaque GTG, FMC) gels, the relevant fragment was excised from the gels, and purified using QIAquick Gel extraction Kit (Qiagen, USA) according to the manufacturer's instructions. The isolated DNA fragment was then ligated to BamHI digested pUC19 and the ligation mixture was used to transform *E. coli* SJ2.

Cells were plated on LB agar plates containing Erythromycin (200 µg/ml) supplemented with X-gal (SIGMA, USA)(5-Bromo-4-chloro-3-indolyl alpha-D-galactopyranoside, 50 µg/ml).

Identification and Characterisation of Positive Clones

The transformed cells were plated on LB agar plates containing Erythromycin (200 µg/ml) supplemented with X-gal (50 µg/ml) and incubated at 37° C. over night. Next day white colonies were rescued by restreaking these onto fresh LB-Erythromycin agar plates and incubated at 37° C. over night. The next day single colonies of each clone were transferred to liquid LB medium containing Erythromycin (200 µg/ml) and incubated overnight at 37° C. with shaking at 250 rpm.

Plasmids were extracted from the liquid cultures using QIAgen Plasmid Purification mini kit (Qiagen, USA) according to the manufacturer's instructions. Five-µl samples of the plasmids were digested with BamHI. The digestion were checked by gelelectrophoresis on a 0.7% agarose gel (NuSieve, FMC). The appearance of two DNA fragments of about 2.7 kb and 3.7 indicated a positive clone. The clone was designated MB293 and the plasmid pMB293.

2)

PMB293 was then EcoRI digested and the 3.8 kb fragment was gelpurified on a 0.7% agarose gel and using QiaQuick gelpurification kit from Qiagen according to the manufacturer. This fragment which constitutes the pE194 with inserted multiple cloningsites (originating from the PCR primers and from MCS of pUC19) was circulised by ligation and used to transform B.subtilis DN1885, transformed cells were selected on LBPG plates containing 5 µg/ml Erythromycin and incubation was done at 33° C. overnight. Clones from this transformation were restreaked and cultivated overnight in TY with 5 µg/ml Erythromycin. From overnight culture broth cells were isolated and plasmids were purified using Qiaquick plasmid kit. Restriction enzyme digestion of the plasmids verified the correctness of the clones. One such clone and plasmid were termed MB333 an pMB333.

3)

The pMB333 was then used as the temperature sensitive plasmid for the construction of a plasmid containing the the Savizyn gene without any promoter. This construct was made as follows.

PCR using the primers #21547 and #21548 and the pSX222 as the template was performed according to these conditions:

1 µl of pSX222 Qiaquick plasmid prep was used for 50 µl PCR amplification in PCR buffer (10 mM Tris-HCl, pH 8.3, 50 mM KCl, 1.5 mM MgCl$_2$, 0.01% (w/v) gelatin) containing 200 µM of each dNTP, 2.5 units of AmpliTaq polymerase (Perkin-Elmer, Cetus, USA) and 100 pmol of each primer:

21547

5'-GCAGCTGCAGGATCCGAATTCGCGGCCGCGC AATCGGTACCATGG-3' (SEQ ID NO:4)

21548

5'-GCAGCGAGCTCAAGCTTCCCGGGCCCAGCC GGTCGACCGCGTTGCCGCTTCTGCG-3' (SEQ ID NO:5)

The PCR reactions was performed using a DNA thermal cycler (Landgraf, Germany). One incubation at 94° C. for 1 min followed by forty cycles of PCR performed using a cycle profile of denaturation at 94° C. for 1 min, annealing at 55° C. for 1 min, and extension at 72° C. for 2 min. Five-µl aliquots of the amplification product was analyzed by electrophoresis in 0.7% agarose gels (NuSieve, FMC).

Subcloning of PCR Fragment

Fortyfive-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. Fifty-µl of the purified PCR fragment was digested with BamHI and ApaI, electrophoresed in 0.8% low gelling temperature agarose (SeaPlaque GTG, FMC) gels, the relevant fragment was excised from the gels, and purified using QIAquick Gel extraction Kit (Qiagen, USA) according to the manufacturer's instructions. Purified fragment was ligated to gelpurified BamHI and ApaI digested pMB333. The ligation was used to transform B.subtilis DN1885. Transformed cells were plated on LBPG agar plates containing 5 µg/ml Erythromycin and incubated overnight at 33° C. Clones were restreaked on similar plates and plasmids were isolated from overnight cultures of clones incubated at 33° C. in TY with 5 µg/ml Erytrhomycin plasmids were isolated using Qiaquick plasmid kit as described by manufacturer. Plasmids were checked by enzymatic digestion using ApaI and BamHI. One correct clone was termed MB339 and the plasmid pMB339.

4)

We wanted to test an easy way of monitoring that hybrid plasmids had formed. Thus we wanted to monitor the forced recombination between the two homologous genes on the two seperate plasmids. This was done by constructing a pE194 derivative having a promoter-lacking Savizyn transcrioptionally fused to an ORF encoding GFP. In this way there would be no expression of GFP (due to lack of promoter upstream of the Savizyn and thus the GFP gene) unless the two homologous genes had recombined and thus getting the GFP under control of the promoter otherwise present on pSX120. The plasmid was constructed by PCR amplifying the GFP gene and introducing it just downstream of the savizyn gene on the pMB339.

The GFP encoding DNA used herein is a derivative of the original wildtype gene, the derivative of GFP was cloned from the DNA construction of the mutant F64L-S65T-GFP which was constructed as described in international patent application WO 97/11094.

The construction of the template plasmid was described in WO 97/11094. The DNA fragment encoding the F64L-S65T-GFP was PCR amplifyed from the E.coli plasmid encoding this gene as follows:

1 µl of pF64L-S65T-GFP Qiaquick plasmid prep was used for 50 µl PCR amplification in PCR buffer (10 mM Tris-HCl, pH 8.3, 50 mM KCl, 1.5 MM MgCl$_2$, 0.01% (w/v) gelatin) containing 200 µM of each dNTP, 2.5 units of AmpliTaq polymerase (Perkin-Elmer, Cetus, USA) and 100 pmol of each primer:

20231 5'-AACTGCAGAAGATGTGGACGCGC-3' (SEQ ID NO:6)

101381

5'-GCCCAATGCATAAACTGCATCCCTTAACTTG TTTTATTTGTATAGTTCATCCATGCCATG-3' (SEQ ID NO:7)

The PCR reactions was performed using a DNA thermal cycler (Landgraf, Germany). One incubation at 94° C. for 1 min followed by forty cycles of PCR performed using a cycle profile of denaturation at 94° C. for 1 min, annealing at 55° C. for 1 min, and extension at 72° C. for 2 min. Five-µl aliquots of the amplification product was analyzed by electrophoresis in 0.7% agarose gels (NuSieve, FMC).

Subcloning of PCR Fragment

Forty-five-µl aliquots of the PCR products generated as described above were purified using QIAquick PCR purification kit (Qiagen, USA) according to the manufacturer's instructions. The purified DNA was eluted in 50 µl of 10 mM Tris-HCl, pH 8.5. The PCR fragment and pMB339 were digested with ClaI and NsiI, gelpurified as above and ligated together. The ligation mixture was used to transform DN1885, transformed cells were plated on LBPG 5 µg/ml Erythromycin. After 18 hours of incubation green flourescent cells were visible as single colonies. One of these were analysed and saved as MB406 and the corresponding plasmid as pMB406. Since the GFP encoding ORF did not have an upstream promoter driving the transcription a possible explanation for the GFP expression could be a read through from a promoter further upstream of the Savizyn-GFP transcriptional fusion, namely the promoter of the repF gene.
5)

In order two abolish any read-through into the ORF of GFP, a transcriptional terminator was inserted between the repF gene and the Savizyn DNA. The terminator was amplified from the pMUTIN-4-MCS plasmid using the following primers and conditions:

1 μl of pMUTIN-4-MCS Qiaquick plasmid prep was used for 50 μl PCR amplification in PCR buffer (10 mM Tris-HCl, pH 8.3, 50 mM KCl, 1.5 mM $MgCl_2$, 0.01% (w/v) gelatin) containing 200 μM of each dNTP, 2.5 units of AmpliTaq polymerase (Perkin-Elmer, Cetus, USA) and 100 pmol of each primer:

102588
   5'-CGGACGGTACCGGTAATGACTCTCTAGCTTG AGGC-3' (SEQ ID NO:8)
102589
   5'-GGGTACAGATCTCCGCGGCGCAAAAAGGCCA TCCGTCAGG-3' (SEQ ID NO:9)

The PCR reactions was performed using a DNA thermal cycler (Landgraf, Germany). One incubation at 94° C. for 60 sec followed by forty cycles of PCR performed using a cycle profile of denaturation at 94° C. for 30 sec, annealing at 55° C. for 30 min, and extension at 72° C. for 1 min. Five-μl aliquots of the amplification product was analyzed by electrophoresis in 0.7% agarose gels (NuSieve, FMC).

The amplified DNA was purified as above and cloned as a KpnI-BglII fragment in pMB406 also BglII and KpnI digested (same procedure for gelpurifying etc. as decribed above). The ligation mixture was used to transform DN1885, transformed cells were plated on LBPG 5 μg/ml Erythromycin. After 18 hours of incubation cells were visible as single colonies. One of these were ananlysed and saved as MB430 and correspondingly the plasmid pMB430. This clone had absolutely no expression of GFP indicating that the cloned terminator in fact worked as anticipated. The resulting sequence of the entire plasmid pMB430 is listed as SEQ NO 1.

Establishing the MB432 Strain

PL1801 Bacillus subtilis was transformed with the two plasmids pMB430 and pSX120 using approximately 1 μg of each plasmid per 100 μl of competent PL1801. The transformed cells were plated onto LBPG-5 μg/ml Erythromycin, incubated overnight at 33° C. Next day colonies were restreaked onto LBPG-5 μg/ml Erythromycin+6 μg/ml Chloramphenicol and incubated overnight at 33° C. Clones were also grown i liquid culture TY-5 μg/ml Erythromycin+6 μg/ml Chloramphenicol overnight at 33° C., plasmids were purified from culture broth and the existence of both pMB430 and pSX120 in the PL1801 strain was verified. This clone was saved and termed MB432.

Example 1
Sequence Shuffling of Two Homologous Sequences Both Coding for the Subtilisin Gene of Savinase The Savinase wt gene (comprised in pSX120) coding for a protease of the subtilisin type was chosen as the target for shuffling of highly homologous genes. A site-directed variant of the Savinase gene (hereafter called Savizyn, comprised in pSX222, where a large number of silent mutations giving new restriction sites are introduced, was used as the shuffling partner to Savinase. The two genes were cloned on two separate compatible plasmids according to the invention. A transcriptionally active Savinase gene was cloned on a plasmid based on the pUB110 origin coding for resistance to chloramphenicol (pSX120, FIG. 4). A promoter less Savizyn gene was cloned on a derivative of the temperature sensitive plasmid pE194 which also codes for resistance to erythromycin (pM430). Two transcription terminators were cloned upstream of the Savizyn gene to prevent any read-through.

In pMB430 the green florescence protein (GFP) was transcriptionally fused to the Savizyn gene in order to be able to visually follow the in-cross and out-cross events between the two plasmids.

B.subtilis strain MB432, pL1801 transformed with the two plasmids pSX120 and pMB430, were taken through two cycles of temperature shifts to induce two consecutive double-cross over events between the homologous genes. Homologous recombination and plasmid hybrid formation was selected on LBPG plates at the restrictive temperature (47–50° C.) in the presence of erythromycin. Under these restrictive conditions, the temperature sensitive plasmid pMB430 is forced into the stable pSX120 plasmid by homologous recombination in the region of Savinase/Savizyn. These colonies where recombination has occurred also becomes fluorescent as a result of the recombination between the two plasmids and concomitant activation of the Savizyn-GFP operon (FIG. 2). Out-cross events were screened by growing the clones in LB-broth at the permissive temperature of 30° C. for two days and plating the cells on LBPG plate with chloramphenicol and erythromycin. The non-fluorescent colonies were restreaked on plates and taken through a second round of temperature cycle as described above.

After the second round of shuffling, plasmid preparations were made from 20 different clones. Competent PL1801 was transformed with each of the 20 plasmid preps and plated on LBPG supplemented with erythromycin. The plates were replicated onto LBPG plates with chloramphenicol and erythromycin to identify unwanted clones where both pSX120 and pMB430 had been transformed. Clones where only the pMB430 plasmid had been transformed were selected for sequencing of the Savizyn region to identify if shuffling had taken place. It is evident from FIG. 6 that recombination between the two genes Savinase and Savizyn had taken place. All of the 12 sequenced clones show some degree of recombination and 4 of these can positively be identified as being result of two consecutive double recombination events. It is important to note that exchange of Savinase and Savizyn sequence can only be observed if the shuffled fragment overlaps a restriction site that is unique for Savizyn. The four clones with a positive evidence for two double recombinations is therefore the minimum number since the recombination could have occurred between two neighbouring restriction sites.

We claim:

1. A process for in vivo recombination of homologous DNA sequences, comprising the steps of:
   (a) providing a cell comprising a population of DNA structures comprising at least two DNA structures, each DNA structure comprising (i) a DNA sequence which is homologous to at least one other DNA sequence in the population and (ii) an origin of replication;
   (b) incubating the cell under conditions which (i) render the origin of replication of at least one of the DNA structures in the population non-functional and the origin of replication of at least one of the DNA structures in the population functional; and (ii) cause a selective pressure so that the cell will grow only if the cell contains the DNA structure having the non-functional origin of replication; wherein formation of a hybrid DNA structure comprising the DNA structure having the non-functional origin of replication and the DNA structure having the functional origin of replication is favored;
   (c) changing the conditions to favor a crossing out event in the hybrid DNA structure of (b); and
   (d) repeating steps (b) and (c) at least once.

2. The process of claim 1, wherein the population includes at least one DNA structure that is a chromosome.

3. The process of claim 1, wherein the population includes at least one DNA structure that is a vector.

4. The process of claim 1, wherein the population includes at least one DNA structure that is a a bacteria vector.

5. The process of claim 1, wherein the population includes at least one DNA structure that is a a bacterial vector which is able to replicate in a Bacillus cell.

6. The process of claim 1, wherein the population includes at least two DNA structures that are vectors.

7. A process for in vivo recombination of homologous DNA sequences, comprising the steps of:
   (a) inserting homologous DNA sequences in at least two different vectors, the at least two vectors having different origins of replication;
   (b) transferring the vectors into a cell;
   (c) incubating the cell under conditions which (i) render the origin of replication of at least one of the vectors non-functional and the origin of replication of at least one of the vectors functional; and (ii) cause a selective pressure so that the cell will grow only if the cell contains the vector having the non-functional origin of replication; wherein formation of a hybrid DNA structure comprising the DNA structure having the nonfunctional origin of replication and the DNA structure having the functional origin of replication is favored;

(d) changing the conditions to favor a crossing out event in the hybrid DNA structure of (b); and (e) repeating steps (c) and (d) at least once.

8. The process of claim 1, wherein the selective pressure involves chemically or physically regulating the origin of replication of the DNA structures.

9. The process of claim 1, wherein at least one origin of replication in the population is temperature sensitive.

10. The process of claim 9, wherein the selective pressure involves a temperature shift.

11. The process of claim 1, wherein the DNA structures include genes comprising selectable markers.

12. The process of claim 11, wherein the selectable markers are antibiotic markers.

13. The process of claim 1, wherein at least one DNA structure in the population is Ori(+).

14. The process of claim 1, wherein at least one DNA structure in the population is Ori(−).

15. The process of claim 1, wherein formation of the hybrid structure is measured in vivo by detecting a protein that is expressed only after the hybrid structure has been formed.

16. The process of claim 15, wherein the protein is a fluorescent protein.

17. The process of claim 16, wherein the fluorescent protein is a Green Florescent protein.

18. The process of claim 1, wherein the crossing out from the hybrid DNA structure is a forced crossing out event.

19. The process of claim 1, wherein the homologous DNA sequences comprise DNA sequences from a DNA library.

20. The process of claim 1, wherein the DNA structures include two or more different sets of homologous DNA sequences.

21. The process of claim 1, wherein the homologous DNA sequences are from at least two different DNA libraries.

22. A process for in vivo recombination of a first set and a second set of homologous DNA sequences, comprising the steps of:

(a) inserting at least one DNA sequence from the first set in a DNA structure containing a temperature resistant origin of replication and a gene for a first marker;

(b) inserting at least one DNA sequence from the second set in a DNA structure containing a temperature sensitive origin of replication and a gene for a second marker;

(c) transferring the DNA structures into a cell;

(d) incubating the cell at a temperature at which both origins of replication are functional, optionally under a selection pressure that favors cells with both marker genes;

(e) shifting the temperature to a temperature, where only the temperature resistant origin of replication is functional; and (f) repeating steps (d)–(e) at least once.

23. A process for in vivo recombination of a first set and a second set of homologous DNA sequences, comprising the steps of:

(a) inserting at least one sequence from the first set in a DNA structure containing a temperature resistant origin of replication and a gene for a first marker;

(b) inserting at least one sequence from the second set in a DNA structure containing a temperature sensitive origin of replication and a gene for a second marker;

(c) transferring the DNA structures into a cell;

(d) incubating the cell at a temperature where only the temperature resistant origin of replication is functional, optionally under a selection pressure that favors cells with both marker genes;

(e) shifting the temperature to a temperature at which both origins of replication are functional; and (f) repeating steps (d)–(e) at least once.

24. The process of claim 1, wherein the cell is defective or transitorily inactivated in the enzymatic mismatch repair system or has a reduced level of mismatch repair.

25. The process of claim 1, wherein the cell is a Gram positive cell.

26. The process of claim 1, wherein the cell is a Staphylococcus cell, a Streptococcus cell, and a Bacillus cell.

27. The process of claim 1, wherein the cell is a *Bacillus subtilis* cell.

28. The process of claim 1, wherein the cell is a Gram negative cell.

29. The process of claim 1, wherein the cell is an Escherichia cell.

30. The process of claim 1, wherein the homologous DNA sequences encode polypeptides.

31. The process of claim 1, wherein the homologous DNA sequences encode enzymes.

32. The process of claim 1, wherein the homologous DNA sequences encode enzymes selected from the group consisting of an amylase, lipase, cutinase, cellulase, oxidase, phytase, and a protease.

* * * * *

SEQUENCE LISTING

<160> NUMBER OF SEQ ID NOS: 9

<210> SEQ ID NO 1
<211> LENGTH: 5313
<212> TYPE: DNA
<213> ORGANISM: Homologous

<400> SEQUENCE: 1

| | | | | | |
|---|---|---|---|---|---|
| gatcagtaca | agaaagatac | tgtatttcat | aaacaggaac | tgcaagaagt | taaggatgag | 60 |
| ttacagaagg | caaataagca | gttacagagt | ggaatagagc | atatgaggtc | tacgaaaccc | 120 |
| tttgattatg | aaaatgagcg | tacaggtttg | ttctctggac | gtgaagagac | tggtagaaag | 180 |
| atattaactg | ctgatgaatt | tgaacgcctg | caagaaacaa | tctcttctgc | agaacggatt | 240 |
| gttgatgatt | acgaaaatat | taagagcaca | gactattaca | cagaaaatca | agaattaaaa | 300 |
| aaacgtagag | agagtttgaa | agaagtagtg | aatacatgga | aagagggta | tcacgaaaaa | 360 |
| agtaaagagg | ttaataaatt | aaagcgagag | aatgatagtt | tgaatgagca | gttgaatgta | 420 |
| tcagagaaat | ttcaagctag | tacagtgact | ttatatcgtg | ctgcgagggc | gaatttccct | 480 |
| gggtttgaga | aagggtttaa | taggcttaaa | gagaaattct | ttaatgattc | caaatttgag | 540 |
| cgtgtgggac | agtttatgga | tgttgtacag | gataatgtcc | agaaggtcga | tagaaagcgt | 600 |
| gagaaacagc | gtacagacga | tttagagatg | tagaggtact | tttatgccga | gaaaactttt | 660 |
| tgcgtgtgac | agtccttaaa | atatacttag | agcgtaagcg | aaagtagtag | cgacagctat | 720 |
| taactttcgg | ttgcaaagct | ctaggatttt | taatggacgc | agcgcatcac | acgcaaaaag | 780 |
| gaaattggaa | taaatgcgaa | atttgagatg | ttaattaaag | acctttttga | ggtctttttt | 840 |
| tcttagattt | tgggggttat | ttaggggaga | aaacataggg | gggtactacg | acctcccccc | 900 |
| taggtgtcca | ttgtccattg | tccaaacaaa | taaataaata | ttgggttttt | aatgttaaaa | 960 |
| ggttgttttt | tatgttaaag | tgaaaaaaac | agatgttggg | aggtacagtg | atggttgtag | 1020 |
| atagaaaaga | agagaaaaaa | gttgctgtta | ctttaagact | tacaacagaa | gaaaatgaga | 1080 |
| tattaaatag | aatcaaagaa | aaatataata | ttagcaaatc | agatgcaacc | ggtattctaa | 1140 |
| taaaaaaata | tgcaaaggag | gaatacggtg | cattttaaac | aaaaaaagat | agacagcact | 1200 |
| ggcatgctgc | ctatctatga | ctaaattttg | ttaagtgtat | tagcaccgtt | attatatcat | 1260 |
| gagcgaaaat | gtaataaaag | aaactgaaaa | caagaaaaat | tcaagaggac | gtaattggac | 1320 |
| atttgtttta | tatccagaat | cagcaaaagc | cgagtggtta | gagtatttaa | aagagttaca | 1380 |
| cattcaattt | gtagtgtctc | cattacatga | tagggatact | gatacagaag | gtaggatgaa | 1440 |
| aaaagagcat | tatcatattc | tagtgatgta | tgagggtaat | aaatcttatg | aacagataaa | 1500 |
| aataattaac | agaagaattg | aatgcgacta | ttccgcagat | tgcaggaagt | gtgaaaggtc | 1560 |
| ttgtgagata | tatgcttcac | atggacgatc | ctaataaatt | taaatatcaa | aaagaagata | 1620 |
| tgatagttta | tggcggtgta | gatgttgatg | aattattaaa | gaaaacaaca | acagatagat | 1680 |
| ataaattaat | taagagaaatg | attgagttta | ttgatgaaca | aggaatcgta | gaatttaaga | 1740 |
| gtttaatgga | ttatgcaatg | aagtttaaat | ttgatgattg | gttcccgctt | ttatgtgata | 1800 |
| actcggcgta | tgttattcaa | gaatatataa | aatcaaatcg | gtataaatct | gaccgataga | 1860 |
| ttttgaattt | aggtgtcaca | agacactctt | ttttcgcacc | agcgaaaact | ggtttaagcc | 1920 |
| gactgcgcaa | aagacgaatt | cgagctcggt | accggtaatg | actctctagc | ttgaggcatc | 1980 |
| aaataaaacg | aaaggctcag | tcgaaagact | gggcctttcg | ttttatctgt | tgtttgtcgg | 2040 |

```
tgaacgctct cctgagtagg acaaatccgc cgctctagct aagcagaagg ccatcctgac    2100
ggatggcctt tttgcgccgc ggagatctaa atattcgtgg tggcgcaagc tttgtaccag    2160
gggaaccgtc gactcaagat gggaatgggc atggcacgca tgtggccggg acgatcgctg    2220
ctttaaacaa ttcgattggc gttcttggcg tagcgccgag cgctgagcta tacgctgtta    2280
aagtcctagg ggcgagcggt tcaggttcgg tcagctcgat tgcccaagga ttggaatggg    2340
cagggaacaa tggcatgcac gttgctaatt tgagtttagg aagcccttcg ccaagtgcca    2400
cactcgagca agctgttaat agcgcgactt ctagaggcgt tcttgttgta gcggcatctg    2460
ggaattcagg tgcaggctca atcagctatc cggcgcgcta tgcgaacgca atggcagtcg    2520
gagctactga tcaaacaac aaccgcgcta gcttttcaca gtatggcgca ggccttgaca    2580
ttgtcgcacc cggggtaaac gtgcagagca catacccagg ttcaacatat gccagcttaa    2640
acggtacatc gatggctact cctcatgttg caggtgcggc cgcccttgtt aaacaaaaga    2700
acccatcttg gtctaatgta caaattcgaa atcatctaaa gaatacggca actagtttag    2760
gaagcacgaa cttgtatgga agcggacttg ttaacgcaga agcggcaacg cgttaaaaat    2820
gaggagggaa gctttatgag taaaggagaa gaacttttca ctggagttgt cccaattctt    2880
gttgaattag atggcgatgt taatgggcaa aaattctctg ttagtggaga gggtgaaggt    2940
gatgcaacat acggaaaact tacccttaaa tttatttgca ctactgggaa gctacctgtt    3000
ccatggccaa cgcttgtcac tactctctct tatggtgttc aatgcttttc tagatacccca    3060 gatcatatga aacagcatga ctttttcaag agtgccatgc ccgaaggtta tgtacaggaa    3120
agaactatat tttacaaaga tgacgggaac tacaagacac gtgctgaagt caagtttgaa    3180
ggtgataccc ttgttaatag aatcgagtta aaaggtattg attttaaaga agatggaaac    3240
attcttggac acaaaatgga atacaattat aactcacata atgtatacat catggcagac    3300
aaaccaaaga atggcatcaa agttaacttc aaaattagac acaacattaa agatggaagc    3360
gttcaattag cagaccatta tcaacaaaat actccaattg gcgatggccc tgtccttttta    3420 ccagacaacc attacctgtc cacgcaatct gccctttcca aagatcccaa cgaaaagaga    3480
gatcacatga tccttcttga gtttgtaaca gctgctggga ttacacatgg catggatgaa    3540
ctatacaaat aaaacaagtt aagggatgca gtttatgcat cccttaactt acttattaaa    3600
taatttatag ctattgaaaa gagataagaa ttgttcaaag ctaatattgt ttaaatcgtc    3660
aattcctgca tgtttaagg aattgttaaa ttgatttttt gtaaatattt tcttgtattc    3720
tttgttaacc catttcataa cgaaataatt atacttttgt ttatctttgt gtgatattct    3780
tgattttttt ctacttaatc tgataagtga gctattcact ttaggtttag gatgaaaata    3840
ttctcttgga accatactta atatagaaat atcaacttct gccattaaaa gtaatgccaa    3900
tgagcgtttt gtatttaata atcttttagc aaacccgtat tccacgatta aataaatctc    3960
attagctata ctatcaaaaa caattttgcg tattatatcc gtacttatgt tataaggtat    4020
attaccatat attttatagg attggttttt aggaaattta aactgcaata tatccttgtt    4080
taaaacttgg aaattatcgt gatcaacaag tttattttct gtagttttgc ataatttatg    4140
gtctatttca atggcagtta cgaaattaca cctctttact aattcaaggg taaaatggcc    4200
ttttcctgag ccgatttcaa agatattatc atgttcattt aatcttatat ttgtcattat    4260
tttatctata ttatgttttg aagtaataaa gttttgactg tgttttatat ttttctcgtt    4320
cattataacc ctctttaatt tggttatatg aattttgctt attaacgatt cattataacc    4380
```

-continued

```
acttattttt tgtttggttg ataatgaact gtgctgatta caaaaatact aaaaatgccc      4440 atatttttc ctccttataa aattagtata attatagcac gagctctgat aaatatgaac       4500
atgatgagtg atcgttaaat ttatactgca atcggatgcg attattgaat aaaagatatg     4560
agagatttat ctaatttctt ttttcttgta aaaaagaaa gttcttaaag gttttatagt      4620
tttggtcgta gagcacacgg tttaacgact taattacgaa gtaaataagt ctagtgtgtt    4680
agactttatg aaatctatat acgtttatat atatttatta tccggaggtg tagcatgtct    4740
cattcaattt tgagggttgc cagagttaaa ggatcaagta atacaaacgg gatacaaaga    4800
cataatcaaa gagagaataa aaactataat aataaagaca taaatcatga ggaaacatat   4860
aaaaattatg atttgattaa cgcacaaaat ataaagtata aagataaaat tgatgaaacg    4920
attgatgaga attattcagg gaaacgtaaa attcggtcag atgcaattcg acatgtggac   4980
ggactggtta caagtgataa agatttcttt gatgatttaa gcggagaaga aatagaacga   5040 tttttaaag atagcttgga gtttctagaa aatgaatacg gtaaggaaaa tatgctgtat     5100
gcgactgtcc atctggatga aagagtccca catatgcact ttggttttgt ccctttaaca   5160
gaggacggga gattgtctgc aaaagaacag ttaggcaaca agaaagactt tactcaatta   5220
caagatagat ttaatgagta tgtgaatgag aaaggttatg aacttgaaag aggcacgtcc   5280
aaagaggtta cagaacgaga acataaagcg atg                                 5313
```

<210> SEQ ID NO 2
<211> LENGTH: 44
<212> TYPE: DNA
<213> ORGANISM: Artificial Sequence
<220> FEATURE:
<223> OTHER INFORMATION: Primer

<400> SEQUENCE: 2
gcagctggat ccgcggccgc gaattcgtct tttgcgcagt cggc         44

<210> SEQ ID NO 3
<211> LENGTH: 51
<212> TYPE: DNA
<213> ORGANISM: Artificial Sequence
<220> FEATURE:
<223> OTHER INFORMATION: Primer

<400> SEQUENCE: 3
gcagctggat ccgggcccgg gaagcttcga ttcacaaaaa ataggcacac g      51

<210> SEQ ID NO 4
<211> LENGTH: 45
<212> TYPE: DNA
<213> ORGANISM: Artificial Sequence
<220> FEATURE:
<223> OTHER INFORMATION: Primer

<400> SEQUENCE: 4
gcagctgcag gatccgaatt cgcggccgcg caatcggtac catgg        45

<210> SEQ ID NO 5
<211> LENGTH: 55
<212> TYPE: DNA
<213> ORGANISM: Artificial Sequence
<220> FEATURE:
<223> OTHER INFORMATION: Primer

<400> SEQUENCE: 5
gcagcgagct caagcttccc gggcccagcc ggtcgaccgc gttgccgctt ctgcg    55

```
<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
aactgcagaa gatgtggacg cgc                                              23

<210> SEQ ID NO 7
<211> LENGTH: 60
<212> TYPE: DNA
<213> ORGANISM: Artificial Sequence
<220> FEATURE:
<223> OTHER INFORMATION: Primer

<400> SEQUENCE: 7
gcccaatgca taaactgcat cccttaactt gttttatttg tatagttcat ccatgccatg      60

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
cggacggtac cggtaatgac tctctagctt gaggc                                 35

<210> SEQ ID NO 9
<211> LENGTH: 40
<212> TYPE: DNA
<213> ORGANISM: Artificial Sequence
<220> FEATURE:
<223> OTHER INFORMATION: Primer

<400> SEQUENCE: 9
gggtacagat ctccgcggcg caaaaaggcc atccgtcagg                            40
```